United States Patent [19]

House

[11] Patent Number: 5,900,226

[45] Date of Patent: May 4, 1999

[54] DRYING AGENTS FOR NON-FOAMED POLYURETHANES

[75] Inventor: David W. House, Arlington Heights, Ill.

[73] Assignee: UOP LLC, Des Plaines, Ill.

[21] Appl. No.: 08/835,717

[22] Filed: Apr. 9, 1997

[51] Int. Cl.[6] .................................................. C01B 39/14
[52] U.S. Cl. .................... 423/700; 423/714; 423/715; 423/DIG. 24
[58] Field of Search ..................... 423/700, 714, 423/715, DIG. 24; 502/85

[56] References Cited

U.S. PATENT DOCUMENTS

| | | | |
|---|---|---|---|
| 2,882,243 | 4/1959 | Milton | 252/455 |
| 3,326,844 | 6/1967 | Gruber | 260/40 |
| 3,506,593 | 4/1970 | Allenbach | 252/455 |
| 3,695,837 | 10/1972 | Sunderland et al. | 423/714 |
| 4,134,965 | 1/1979 | Rein et al. | |
| 4,222,995 | 9/1980 | Roebke et al. | |
| 4,251,427 | 2/1981 | Recker et al. | 260/37 |
| 4,654,316 | 3/1987 | Barri et al. | 502/85 |
| 4,857,584 | 8/1989 | Vandermeersch et al. | 524/791 |
| 4,987,109 | 1/1991 | Kao et al. | 502/85 |
| 5,401,785 | 3/1995 | Kumagai et al. | 521/112 |

FOREIGN PATENT DOCUMENTS

| | | |
|---|---|---|
| 0346604B1 | 3/1989 | European Pat. Off. . |
| 327735 | 8/1989 | European Pat. Off. ................. 502/85 |

OTHER PUBLICATIONS

Patterson, "A German–English Dictionary," pp. 401 and 478, 1950.

*Primary Examiner*—Mark L. Bell
*Assistant Examiner*—David Sample
*Attorney, Agent, or Firm*—Thomas K. McBride; John G. Tolomei; Richard P. Silverman

[57] ABSTRACT

Mild acid treatment of zeolite 3A molecular sieve to modify the pH of the surface of the molecular sieve to a pH ranging between 9.5 and 11 was found to significantly minimize the effect of the zeolite 3A on the pot life of non-foamed polyurethanes. Increases in pot life over untreated zeolite 3A molecular sieve were dramatic (about 400%) with less than 5% reduction in water adsorption capacity.

7 Claims, No Drawings

DRYING AGENTS FOR NON-FOAMED POLYURETHANES

FIELD OF THE INVENTION

This invention relates to a process for preparing non-foamed, or non-cellular polyurethanes. More particularly, the invention relates to the incorporation of a surface-modified zeolitic dehydrating agent into the non-foamed polyurethane plastics to minimize the formation of gas bubbles in polyurethane resin formulations.

BACKGROUND OF THE INVENTION

Non-foamed polyurethane is widely used in the manufacture of lacquers, adhesives, sealants, molded products, films, and coatings. In these applications, the appearance and the mechanical properties can be seriously affected by the presence of gas bubbles in the product. Substantially non-porous polyurethane plastics are generally prepared by reacting an organic polyisocyanate with an organic compound such as a polyol containing active hydrogen containing groups, polyamine compounds, or polyhydroxylated compounds. Polyols or polyhydroxylated compounds are known to absorb water and generally are the source for the introduction of water into the formulation. Moisture is introduced either in the polyhydroxylated compound or in some other ingredient, and this moisture can react with the organic polyisocyanate to produce urea linkages and carbon dioxide. The urea linkages are strong and usually desirable; however, the carbon dioxide causes bubbles to appear in the product. In many cases, the presence of bubbles in the product weakens the structure and may render the product unsatisfactory. In practice, the reaction is carried out at ambient temperature by simply mixing the two components, each containing one of the two reagents, at least one of the components being liquid at ambient temperature. In some applications, especially in producing elastomers, the reaction temperature may be as high as 110° C. The mixture remains liquid or at least fluid during a certain period of time, which permits its use. This period or working time, which precedes the curing of the product, is commonly called the pot life.

Since it is known that the general appearance and the mechanical properties of polyurethane can be improved by incorporating mineral fillers which are inert with respect to the reagents and do not affect their polycondensation, the idea of using dehydrating agents and more particularly zeolites as the additional filler for the component containing the hydroxylated reagent was exploited. Other materials including pigments, catalysts, and solvents may also be incorporated into the polyurethane and are generally combined with the polyhydroxylated compound prior to the reaction.

This type of filler proves to be advantageous for any application of polyurethane in the form of thin films, paints, lacquers, floor and wall coverings because it neutralizes the diffusion of the ambient humidity into the polyurethane during polymerization. Differential curing of the upper layer, which is the source of cracking of the finished product, is thus avoided.

However, the zeolites which have been used for dehydration include the zeolites 4A, 5A, and 10A which possess the highly unfavorable property of adsorbing nitrogen from the air at ambient temperatures, and the desorption of this nitrogen caused by the exothermic nature of the polymerization reaction again creates undesirable microbubbles. U.S. Pat. No. 3,326,844, hereby incorporated by reference, discloses the use of such molecular sieve zeolites in polyurethane compositions and is relied upon for examples of polyols, polyamines, and other organic compounds containing active hydrogen containing groups which are reactive with an isocyanate group suitable for inclusion in polyurethane compositions.

U.S. Pat. No. 4,857, 584 to Vandermeersch et al. discloses the problem that the above mentioned zeolites, in addition to adsorbing water, also tend to adsorb nitrogen from the air particularly when the polyhydroxylated component is stored after the addition of the zeolite. During the polymerization reaction, this nitrogen is released resulting in small bubbles in the finished product. Vandermeersch et al. propose to increase pot life by employing a cation exchanged form of zeolite 3A to avoid the problem of the nitrogen adsorption and to reduce the known reactivity of 3A zeolite in the polyhydroxylated compound during storage.

European Patent No. 0 346 604B1 discloses the use of a potassium zeolite 3A which has been treated with a strong acid to obtain a pH of between 7.5 to 9.5, as a dehydrating agent in polyurethane formulations. The pH of the acid treated potassium zeolite 3A is measured in an aqueous suspension according to DIN ISO 787/IX. The European disclosure indicated an increase in pot life when the pH of the zeolite 3A is reduced to a pH in the 7.5 to 9.5 range.

Currently, zeolite 3A is the most widely used zeolite for moisture scavenging in non-foamed polyurethane formulations. Zeolite 3A which has an alkaline surface is generally regarded as being reactive to polymerization reactions. Severe acid treatment of the zeolite 3A to significantly reduce the surface pH of zeolites may also change the crystal structure which would reduce the capacity of the zeolite to adsorb water. Methods are sought to produce a zeolitic composition which adsorbs a minimum of air and is essentially non-reactive in the polyhydroxylated compound as evidenced by a minimal impact on pot life of the polyurethane resin.

SUMMARY OF THE INVENTION

It was found that a non-foamed or non-cellular polyurethane formulation with an acceptable pot life can be obtained by the use of a surface-modified zeolite 3A. Although the surface of surface-modified zeolite 3A is passivated, the vast majority of the zeolite is potentially still very active as a catalyst for the polyurethane reaction. Nonetheless, the surface-modified 3A zeolite no longer significantly catalyzes the polyurethane reaction after the treatment of the surface. The surface-modified zeolite 3A still retained its high water adsorption capacity, but the significantly reduced reactivity, surprisingly, produced little detrimental effect on pot life. The surface-modified zeolite 3A material was obtained by acid washing zeolite 3A with a dilute acid solution to obtain a surface pH of between 9.5 and 11 without compromising the crystal structure of the zeolite or reducing the ability of the zeolite to adsorb water. Preferably, the dilute acid solution is an aqueous solution of any organic or mineral acid such as an acid selected from the group consisting of hydrochloric, nitric, sulfric, phosphoric, citric, and acetic acids wherein the dilute acid concentration ranges from about 0.01M to about 0.1M. Surprisingly, it was found that the pot life of the surface-modified 3A zeolite increased by over 400 percent compared to the untreated zeolite 3A molecular sieve.

In one embodiment, the present invention is a process for preparing non-foamed polyurethanes comprising reacting a mixture comprising a polyisocyanate, a polyhydroxyl compound, and an adsorbent comprising a zeolite molecular sieve wherein the zeolite molecular sieve comprises a surface-modified potassium 3A zeolite having a pH ranging between about 9.5 and about 11. The mixture may also comprise a polyamine compound or a blend of polyhydroxyl compounds and polyamines.

DETAILED DESCRIPTION OF THE INVENTION

In the preparation of the novel zeolites of this invention, the starting material is the sodium form of zeolite A as described in U.S. Pat. No. 2,882,243 to Robert M. Milton, hereby incorporated by reference. The composition of the sodium form of zeolite A is defined in terms of molar ratios of oxides such as

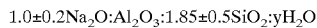
$1.0 \pm 0.2 Na_2O:Al_2O_3:1.85 \pm 0.5 SiO_2:yH_2O$ wherein y has a value from zero to about 6. Using the sodium zeolite A as the starting material, the replacement of the required proportion of the sodium ions by ions of potassium can be accomplished by conventional ion exchange such as immersing or washing the sodium zeolite A crystals with an aqueous solution of potassium salts such as the sulfate, hydroxide, nitrate, and chloride forms. The duration of the above treatment and salt concentrations are selected so that the cation content in terms of per equivalent of Al of the final 3A product, preferably, is from about 30 to about 50 equivalent percent potassium to Al, with the remainder being sodium cations. More preferably, the cation content of the 3A zeolite product is from about 35 to about 45 equivalent percent potassium. In this form, the pH of the 3A zeolite surface is about 11.7.

In the process of the present invention, the zeolite 3A can be acid treated in any number of different ways. One method for acid treating the zeolite 3A is to acid wash the zeolite 3A powder following the potassium ion exchange step. The particle size of zeolite 3A powder is generally in the range of 1 to 15 μm or larger. The resulting slurry is filtered and activated in the conventional manner. Generally, activation is performed by dehydrating the material by heating at temperatures between 250° C. and a maximum of about 400° C. The acid employed to wash the zeolite may be selected from the group consisting of hydrochloric, nitric, sulfuric, phosphoric, citric, and acetic acid. The acid is employed in dilute form. Preferably, the concentration of the acid employed to treat the zeolite is less than about 0.1M in aqueous solution. It was found that the surface passivation by the dilute acid is almost instantaneous. Preferably, the zeolite 3A is exposed to the dilute acid solution for a time less than about 2 hours; and more preferably, the zeolite 3A is exposed to the dilute acid solution for a time ranging between about 0.01 hour and about 1.5 hours; and most preferably, the zeolite 3A is exposed to the dilute acid solution for a time less than about 10 minutes. It is believed that, by the use of dilute acid and a short contact time, the surface of the zeolite 3A is passivated to a pH ranging from about 8 to about 11 without reducing the capacity of the zeolite to adsorb water. Preferably, the surface of the zeolite 3A is passivated to a pH ranging from about 9.5 to about 11, and more preferably, the surface of the zeolite 3A is passivated to a pH ranging from about 9.5 to about 10.5. In fact, dilute acid treatment of the zeolite 3A using 0.05M HCl and 0.05M $HNO_3$ produced a material virtually identical to the untreated sieve with respect to water adsorption capacity. It is believed that the range of the acid strength of the dilute acid is somewhat critical in that the acid strength must be sufficient to passivate the surface of the zeolite without modifying the internal crystal structure which would result in reduced moisture adsorption.

Example

The invention will be further clarified by a consideration of the following examples which are intended to be purely exemplary of the use of the invention.

Example I

Samples of 3A zeolite molecular sieve powder ranging in size from 1–15 μm (3.6 μm median size) in approximately 4 gram lots were combined with approximately 36 grams of dilute acid solution to form a 10 wt-% slurry of the sieve in the acid. After about 30 minutes of contact time, the sieve was filtered, air dried, and calcined at a temperature of about 650° C. The acids employed as the dilute acid solution include sulfuric acid, hydrochloric acid, phosphoric, acetic, citric, and nitric acid at an acid strength of 0.05M and 0.10M. The resulting pH of the sieve sample was determined by preparing a 10 weight percent slurry of the sieve in distilled water and measuring the pH of the resulting slurry. The resulting pH of the 3A zeolite molecular sieve is shown in Table 1. Untreated, the pH of the 3A zeolite molecular sieve was about 11.7.

TABLE 1

| pH of 3A ZEOLITE Following DILUTE ACID TREATMENT | | |
|---|---|---|
| DILUTE ACID: | 0.05M Solution | 0.10M Solution |
| SULFURIC ACID | 8.67 | 8.18 |
| HYDROCHLORIC ACID | 9.91 | 8.88 |
| NITRIC ACID | 9.56 | 9.15 |
| PHOSPHORIC ACID | — | 9.64 |
| ACETIC ACID | — | 10.2 |
| CITRIC ACID | — | 10.1 |

Example II

The pot life of a two component polyurethane formulation with the addition of a molecular sieve was determined according to the following procedure. Approximately 26 grams of dry, activated molecular sieve is admixed with about 26 grams of castor oil in a plastic cup and thoroughly mixed using a high-torque stirrer for about 3 minutes to produce about 50 grams of paste. The resulting paste is allowed to stand overnight to equilibrate and overcome the heat of adsorption. The paste in the cup is adjusted to about 50.0 grams, and 9.85 grams (index 100) of PAPI 27 ( a poly-MDI available from Dow Chemical or similar isocyanate) is added. The isocyanate mixture is stirred for about one minute at about 240 revolutions per minute. The mixture is then periodically tested for pot life using the "string time" test. In the string time test, a clean glass rod or thermometer is used to touch the polymer mixture and pull a string from the polymer to a length of about 2.5 cm. If the resulting string of polymer does not break for at least 10 seconds, then the pot life has been reached. Table 2 shows the dramatic effect of the dilute acid treatment on the 3A zeolite treated with 0.05M nitric acid for 30 minutes in a 10% slurry. The pot life surprisingly improved by over 400 percent.

TABLE 2

EFFECT OF ACID TREATMENT ON POT LIFE

|  | pH | POT LIFE, MINUTES |
|---|---|---|
| UNTREATED 3A | 11.7 | 14 |
| ACID TREATED 3A | 9.56 | 59 |

Example III

The ability of the acid treated zeolite 3A molecular sieve to adsorb moisture was measured on a McBain balance in the conventional manner and compared to the untreated 3A zeolite molecular sieve. The results of this analysis are shown in Table 3. The dilute acid treatment of the 3A zeolite molecular sieve appears to effectively treat the surface of the sieve without significantly reducing the capacity of the sieve to adsorb water. The dilute acid treatment with an acidconcentration of 0.05M with hydrochloric and nitric acids resulted in about a 5% reduction in moisture capacity. Increasing the acid strength for hydrochloric and nitric acid to a 0.1M solution resulted in about a 30% reduction in moisture capacity, indicating some degradation in the crystal structure of the zeolite. It was discovered that decreasing the acid strength to 0.03M was not sufficient to effectively passivate the surface of the sieve.

TABLE 3

MOISTURE CAPACITY OF ACID TREATED 3A

|  | MOISTURE CAPACITY, WT-% | % OF UNTREATED CAPACITY |
|---|---|---|
| UNTREATED 3A | 24.3 | 100 |
| 0.05M $H_2SO_4$ | 16.9 | 70 |
| 0.10M $H_2SO_4$ | 11.9 | 49 |
| 0.05M HCl | 23.3 | 96 |
| 0.10M HCl | 17.7 | 73 |
| 0.05M $HNO_3$ | 22.9 | 94 |

TABLE 3-continued

MOISTURE CAPACITY OF ACID TREATED 3A

|  | MOISTURE CAPACITY, WT-% | % OF UNTREATED CAPACITY |
|---|---|---|
| 0.07M $HNO_3$ | 20.7 | 85 |
| 0.10M $HNO_3$ | 17.4 | 72 |

We claim:

1. A process for preparing a surface-modified potassium 3A zeolite comprising: contacting a potassium 3A zeolite with a dilute aqueous acid solution, said dilute aqueous acid solution having an acid concentration less than about 0.1M for a time period less than about 2 hours to provide the surface-modified potassium 3A zeolite having a pH ranging between 9.6 and about 11.

2. The process of claim 1 wherein the time period ranges between 1 minute and about 30 minutes.

3. The process of claim 1 wherein the dilute aqueous acid solution is selected from the group consisting of solutions of hydrochloric, nitric, sulfuric, phosphoric, citric, and acetic acids.

4. The process of claim 1 wherein the acid solution is a dilute aqueous solution having a concentration of acid in solution that ranges from about 0.01M to about 0.1M.

5. The process of claim 1 wherein the acid solution is a dilute aqueous solution of HCl having a concentration of acid in solution that ranges from about 0.05 to about 0.1M HCl.

6. The process of claim 1 wherein the acid solution is a dilute aqueous solution of nitric acid having a concentration of acid in solution that ranges from about 0.05 to 0.1M nitric acid.

7. The process of claim 1 wherein the pH of the surface-modified potassium 3A zeolite ranges between 9.6 and 10.5.

* * * * *